United States Patent
Vijayendran et al.

(10) Patent No.: US 10,562,961 B2
(45) Date of Patent: *Feb. 18, 2020

(54) ASSAYS FOR IGFBP7 HAVING IMPROVED PERFORMANCE IN BIOLOGICAL SAMPLES

(71) Applicant: ASTUTE MEDICAL, INC., San Diego, CA (US)

(72) Inventors: Ravi A. Vijayendran, San Diego, CA (US); Srivatsa Venkatasubbarao, Torrance, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/818,669

(22) Filed: Nov. 20, 2017

(65) Prior Publication Data

US 2018/0066045 A1    Mar. 8, 2018

Related U.S. Application Data

(63) Continuation of application No. 15/035,205, filed as application No. PCT/US2014/064327 on Nov. 6, 2014, now Pat. No. 9,822,172.

(60) Provisional application No. 61/900,942, filed on Nov. 6, 2013, provisional application No. 62/054,324, filed on Sep. 23, 2014, provisional application No. 62/064,380, filed on Oct. 15, 2014.

(51) Int. Cl.

| | |
|---|---|
| *C07K 16/18* | (2006.01) |
| *G01N 33/74* | (2006.01) |
| *G01N 33/68* | (2006.01) |
| *C12N 5/10* | (2006.01) |
| *C12N 5/12* | (2006.01) |
| *C07H 21/04* | (2006.01) |

(52) U.S. Cl.
CPC ......... *C07K 16/18* (2013.01); *G01N 33/6893* (2013.01); *G01N 33/74* (2013.01); *C07K 2317/10* (2013.01); *C07K 2317/34* (2013.01); *C07K 2317/56* (2013.01); *G01N 2333/4745* (2013.01); *G01N 2800/347* (2013.01)

(58) Field of Classification Search
None
See application file for complete search history.

(56) References Cited

U.S. PATENT DOCUMENTS

| | | |
|---|---|---|
| 2002/0132983 A1 | 9/2002 | Junghans |
| 2006/0073514 A1 | 4/2006 | Dedera et al. |
| 2006/0263907 A1 | 11/2006 | Zweig |
| 2012/0045391 A1* | 2/2012 | Stanimirovic ..... A61K 49/0032 424/1.49 |

FOREIGN PATENT DOCUMENTS

| | | |
|---|---|---|
| WO | WO 92/11383 | 7/1992 |
| WO | WO 2007/008547 | 1/2007 |
| WO | WO 2008/089994 | 7/2008 |
| WO | WO 2010/043037 | 4/2010 |
| WO | WO 2010/127294 | 11/2010 |
| WO | WO 2011/097539 | 8/2011 |
| WO | WO 2012/027723 | 3/2012 |
| WO | WO 2013/067517 | 5/2013 |

OTHER PUBLICATIONS

Dominguez et al., A Combined Approach for Gene Discovery Identifies Insulin-Like Growth Factor-Binding Protein-Related Protein 1 as a New Gene Implicated in Human Endometrial Receptivity. J Clin Endocrinol Metab. Apr. 2003;88(4):1849-1857.

Lopez-Bermejo et al., Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues. J Clin Endocrinol Metab. Jul. 2003;88(7):3401-3408.

Office Action issued by the JPO in Japanese Patent Application 2016-552481 dated Aug. 28, 2018—incl Engl lang transl (7 pages total).

Iqbal et al., "Molecular imaging of glioblastoma multiforme using anti-insulin-like growth factor-binding protein-7 single-domain antibodies," British Journal of Cancer, Nov. 9, 2010, 103(10):1606-1616.

Kutsukake et al., "Circulating IGF-binding protein 7 (IGFBP7) levels are elevated in patients with endometriosis or undergoing diabetic hemodialysis," Reproductive Biology and Endocrinology, 2008, 6(54):1-6.

Extended European Search Report dated Aug. 23, 2017, issued in European application (No. 14860878.9).

International Search Report and Written Opinion dated Apr. 8, 2015, in PCT/US2014/064327.

Official action dated Dec. 20, 2018, issued in Chinese application (No. 201480066318.8).

Official action dated Jan. 31, 2018, issued in Eurasian application (No. 201690731).

Official Action dated Aug. 21, 2018 issued in European application (No. 14860878.9).

Partial Supplementary Search Report dated May 15, 2017, issued in European application (No. 14860878.9).

(Continued)

*Primary Examiner* — Marianne P Allen
(74) *Attorney, Agent, or Firm* — Womble Bond Dickinson (US) LLP

(57) ABSTRACT

The invention provides IGFBP7 immunoassays with improved clinical performance, particularly when used in the evaluation of renal injuries. The immunoassays rely on the selection and use of antibodies and antibody pairs that exhibit improved assay performance when used in complex clinical specimens such as biological fluids, and particularly when used in rapid assay formats such as lateral flow test devices.

14 Claims, No Drawings

Specification includes a Sequence Listing.

(56) References Cited

OTHER PUBLICATIONS

Anonymous, "IGFBP-3 ELISA: Enzyme-Immunoassay for Quantitative Determination of Insulin-Like-Growth-Factor Binding Protein-3", May 4, 2006, pp. 1-25, XP009507630, Retrieved from the Internet: URL: https://search.cosmobio.co.jp/cosmo_search_p/search_gate2/docs/MDA_/E03.20090709.pdf.
Extended European Search Report dated Aug. 20, 2019, issued in European application (No. 19158290.7).
Official action dated Jul. 23, 2019, issued in Japanese application (No. 2016-552481).

\* cited by examiner

SEQUENCE LISTING

```
<160> NUMBER OF SEQ ID NOS: 12

<210> SEQ ID NO 1
<211> LENGTH: 26
<212> TYPE: PRT
<213> ORGANISM: Homo sapiens

<400> SEQUENCE: 1

Leu Ile Trp Asn Lys Val Lys Arg Gly His Tyr Gly Val Gln Arg Thr
1               5                   10                  15

Glu Leu Leu Pro Gly Asp Arg Asp Asn Leu
            20                  25

<210> SEQ ID NO 2
<211> LENGTH: 20
<212> TYPE: PRT
```

```
<213> ORGANISM: Homo sapiens

<400> SEQUENCE: 2

Ser Ser Ser Ser Ser Asp Thr Cys Gly Pro Cys Glu Pro Ala Ser Cys
1               5                   10                  15

Pro Pro Leu Pro
            20

<210> SEQ ID NO 3
<211> LENGTH: 9
<212> TYPE: PRT
<213> ORGANISM: Homo sapiens

<400> SEQUENCE: 3

Thr Glu Leu Leu Pro Gly Asp Arg Asp
1               5

<210> SEQ ID NO 4
<211> LENGTH: 5
<212> TYPE: PRT
<213> ORGANISM: Homo sapiens

<400> SEQUENCE: 4

Glu Pro Ala Ser Cys
1               5

<210> SEQ ID NO 5
<211> LENGTH: 282
<212> TYPE: PRT
<213> ORGANISM: Homo sapiens

<400> SEQUENCE: 5

Met Glu Arg Pro Ser Leu Arg Ala Leu Leu Gly Ala Ala Gly Leu
1               5                   10                  15

Leu Leu Leu Leu Leu Pro Leu Ser Ser Ser Ser Ser Asp Thr Cys
                20                  25                  30

Gly Pro Cys Glu Pro Ala Ser Cys Pro Pro Leu Pro Pro Leu Gly Cys
                35                  40                  45

Leu Leu Gly Glu Thr Arg Asp Ala Cys Gly Cys Cys Pro Met Cys Ala
        50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
                100                 105                 110

Cys Lys Ser Arg Tyr Pro Val Cys Gly Ser Asp Gly Thr Thr Tyr Pro
                115                 120                 125

Ser Gly Cys Gln Leu Arg Ala Ala Ser Gln Arg Ala Glu Ser Arg Gly
                130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
                180                 185                 190

Trp Asn Lys Val Lys Arg Gly His Tyr Gly Val Gln Arg Thr Glu Leu
                195                 200                 205
```

```
Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
        275                 280

<210> SEQ ID NO 6
<211> LENGTH: 16
<212> TYPE: PRT
<213> ORGANISM: Homo sapiens

<400> SEQUENCE: 6

Tyr Gly Val Gln Arg Thr Glu Leu Leu Pro Gly Asp Arg Asp Asn Leu
1               5                   10                  15

<210> SEQ ID NO 7
<211> LENGTH: 16
<212> TYPE: PRT
<213> ORGANISM: Homo sapiens

<400> SEQUENCE: 7

Leu Ile Trp Asn Lys Val Lys Arg Gly His Tyr Gly Val Gln Arg Thr
1               5                   10                  15

<210> SEQ ID NO 8
<211> LENGTH: 20
<212> TYPE: PRT
<213> ORGANISM: Homo sapiens

<400> SEQUENCE: 8

Ser Ser Ser Ser Ser Asp Thr Cys Gly Pro Cys Glu Pro Ala Ser Cys
1               5                   10                  15

Pro Pro Leu Pro
            20

<210> SEQ ID NO 9
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Glu Thr Tyr Leu His Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Arg Thr Asp Phe Thr Leu Lys Ile
65                  70                  75                  80

Ser Arg Val Glu Ala Glu Asp Leu Gly Val Tyr Tyr Cys Ala Gln Gly
                85                  90                  95
```

Thr His Phe Pro His Thr Phe Gly Gly Gly Thr Lys Leu Glu
            100                 105                 110

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Asp Tyr
            20                  25                  30

Ser Ile His Trp Val Lys Gln Ala Pro Gly Lys Gly Leu Lys Trp Met
        35                  40                  45

Gly Leu Ile Asn Thr Glu Thr Gly Glu Pro Ile Tyr Val Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Thr Ala Thr Tyr Phe Cys
                85                  90                  95

Ala Arg Ala Tyr Tyr Trp Ala Tyr Trp Gly Gln Gly Thr Leu Val
            100                 105                 110

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Glu Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Ser Pro Phe Thr
                85                  90                  95

Phe Gly Ser Gly Thr Lys Leu Glu Ile Lys Arg
            100                 105

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

-continued

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Lys Lys Tyr
            20                  25                  30
Gly Met Asn Trp Val Lys Gln Ala Pro Gly Lys Gly Leu Lys Trp Met
        35                  40                  45
Gly Trp Ile Asn Thr Tyr Thr Gly Glu Pro Ile Tyr Ala Asp Asp Phe
    50                  55                  60
Lys Gly Arg Phe Ala Phe Ser Leu Glu Thr Ser Ala Ser Thr Ala Tyr
65                  70                  75                  80
Leu Gln Ile Ser Asn Leu Lys Asn Glu Asp Thr Ala Thr Tyr Phe Cys
            85                  90                  95
Ala Arg Glu Glu Tyr Gly Pro Phe Tyr Ala Met Asp Tyr Trp Gly Gln
            100                 105                 110
Gly Thr Ser Val Thr Val Ser Ser
        115                 120
```

US 10,562,961 B2

ASSAYS FOR IGFBP7 HAVING IMPROVED PERFORMANCE IN BIOLOGICAL SAMPLES

CROSS-REFERENCE TO RELATED APPLICATIONS

The present invention is a continuation of U.S. patent application Ser. No. 15/035,205, filed May 6, 2016, now U.S. Pat. No. 9,822,172, issued Nov. 21, 2017, which is the U.S. national phase of International Patent Application No. PCT/US2014/064327, filed Nov. 6, 2014, which designated the U.S. and application claims the benefit of U.S. Provisional Application No. 61/900,942, filed Nov. 6, 2013, and to U.S. Provisional Application No. 62/054,324, filed Sep. 23, 2014, and to U.S. Provisional Application No. 62/064,380, filed Oct. 15, 2014, each of which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Nov. 20, 2017, is named ASTM_0004_CT_SeqListing.txt and is 9 kilobytes in size.

BACKGROUND

The following discussion of the background of the invention is merely provided to aid the reader in understanding the invention and is not admitted to describe or constitute prior art to the present invention.

IGFBP7 (human precursor Swiss Prot entry Q16270) is a secreted protein which is involved in regulation of of insulin-like growth factor expression in tissue and which modulates IGF binding to its receptors. It also reportedly stimulates prostacyclin production and cell adhesion. IGFBP7 suppresses growth and colony formation of prostate and breast cancer cell lines through an IGF independent mechanism, which causes a delay in the G1 phase of the cell cycle, and increased apoptosis. IGFBP7 is expressed in a wide range of normal human tissues and it usually shows reduced expression in cancer cell lines of prostate, breast, colon, and lung origin.

In addition, WO2011/097539 and WO2011/075744, each of which is hereby incorporated by reference in its entirety including all tables, figures and claims, describe the use of IGFBP7 for evaluating the renal status of a subject both individually and in multimarker panels. In particular, IGFBP7 levels measured by immunoassay are shown to correlate to risk stratification, diagnosis, staging, prognosis, classifying and monitoring of the renal status.

Signals obtained from specific binding assays such as immunoassays are a direct result of complexes formed between one or more binding species (e.g., antibodies) and the target biomolecule (i.e., the analyte) and polypeptides containing the necessary epitope(s) to which the antibodies bind. Immunoassays are often able to "detect" an analyte; but because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. While such assays may detect the full length biomarker and the assay result be expressed as a concentration of a biomarker of interest, the signal from the assay is actually a result of all such "immunoreactive" polypeptides present in the sample. Such binding assays may also detect immunoreactive polypeptides present in a biological sample that are complexed to additional species, such as binding proteins, receptors, heparin, lipids, sugars, etc., provided that those additional species do not interfere in binding between the binding species and the target biomolecule. Typically, however, specific binding assays are formulated using purified analyte, and complex formation and fragmentation patterns are not considered. This is particularly true where the identity of such additional binding species are unknown.

SUMMARY

It is an object of the invention to provide IGFBP7 immunoassays with improved clinical performance, particularly when used in the evaluation of renal injuries. Specifically, we describe the selection and use of antibodies and antibody pairs that exhibit improved assay performance when used in complex clinical specimens such as biological fluids, and particularly when used in rapid assay formats.

In a first aspect, the present invention relates to a monoclonal antibody which specifically binds human IGFBP7 and is suitable for use in a sandwich immunoassay. The antibody specifically binds to a polypeptide consisting of LIWNKVKRGHYGVQRTELL PGDRDNL (SEQ ID NO: 1) or SSSSSDTCGPCEPASCPPLP (SEQ ID NO: 2).

In a related aspect, the present invention relates to an antibody pair which specifically binds human IGFBP7 and is suitable for use in a sandwich immunoassay, the antibody pair comprising a first monoclonal antibody which specifically binds to a polypeptide consisting of LIWNKVKRGHYGVQRTELLPGDRDNL (SEQ ID NO: 1) and a second monoclonal antibody which specifically binds to a polypeptide consisting of SSSSSDTCGPCEPASCPPLP (SEQ ID NO: 2).

In another related aspect, the present invention relates to a monoclonal antibody which specifically binds human IGFBP7 and is suitable for use in a sandwich immunoassay. The antibody specifically binds to a conformational epitope of IGFBP7. Conformational epitopes are formed by residues that are sequentially discontinuous but close together in three-dimensional space in the IGFBP7 protein. An example of such an antibody, referred to as 1D6, is described below.

In a related aspect, the present invention relates to an antibody pair which specifically binds human IGFBP7 and is suitable for use in a sandwich immunoassay, the antibody pair comprising a first monoclonal antibody which specifically binds to a conformational epitope of IGFBP7, and a second monoclonal antibody which specifically binds to a polypeptide consisting of LIWNKVKRGHYGVQRTELLPGDRDNL (SEQ ID NO: 1) or SSSSSDTCGPCEPASCPPLP (SEQ ID NO: 2).

In certain embodiments, an antibody of the present invention comprises one or both of (i) a light chain variable region having an amino acid sequence of SEQ ID NO: 9 or a sequence at least 90% identical to SEQ ID NO: 9, and (ii) a heavy chain variable region having an amino acid sequence of SEQ ID NO: 10 or a sequence at least 90% identical to SEQ ID NO: 10, wherein the antibody specifically binds human IGFBP7. In preferred embodiments, the antibody is that which is referred to herein as IC9E4.1.

In other embodiments, an antibody of the present invention comprises one or both of (i) a light chain variable region having an amino acid sequence of SEQ ID NO: 11 or a sequence at least 90% identical to SEQ ID NO: 11, and (ii) a heavy chain variable region having an amino acid sequence of SEQ ID NO: 12 or a sequence at least 90% identical to SEQ ID NO: 12, wherein the antibody specifically binds human IGFBP7. In preferred embodiments, the antibody is that which is referred to herein as 1D6.

In certain embodiments, an antibody pair of the present invention comprises (i) a first antibody which comprises one or both of (i) a light chain variable region having an amino acid sequence of SEQ ID NO: 11 or a sequence at least 90% identical to SEQ ID NO: 11, and (ii) a heavy chain variable region having an amino acid sequence of SEQ ID NO: 12 or a sequence at least 90% identical to SEQ ID NO: 12, wherein the antibody specifically binds human IGFBP7; and (ii) a second antibody which comprises one or both of (i) a light chain variable region having an amino acid sequence of SEQ ID NO: 9 or a sequence at least 90% identical to SEQ ID NO: 9, and (ii) a heavy chain variable region having an amino acid sequence of SEQ ID NO: 10 or a sequence at least 90% identical to SEQ ID NO: 10, wherein the antibody specifically binds human IGFBP7. In preferred embodiments, the antibody pair comprises a first antibody referred to herein as 1D6 and a second antibody referred to herein as IC9E4.1.

The phrase "specifically binds to a polypeptide consisting of" a particular sequence as used herein is not intended to mean that the antibody does not bind to a longer polypeptide comprising the sequence, or to a shorter polypeptide that is a subset of the sequence. Rather, this phrase is simply intended to mean that the antibody will bind to the particular recited polypeptide.

Antibodies for use in the claimed methods may be obtained from a variety of species. For example, the antibodies of the present invention may comprise immunoglobulin sequences which are rabbit, mouse, rat, guinea pig, chicken, goat, sheep, donkey, human, llama or camelid sequences, or combinations of such sequences (so-called chimeric antibodies). Antibodies for use in the present invention may be identified by their performance in immunoassays, and then further characterized by epitope mapping in order to understand the epitopes which are relevant to that performance.

Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Preferably, an epitope for each antibody is contained within SEQ ID NO: 1 or SEQ ID NO: 2, which is a sequence obtained from the human IGFBP7 sequence. In certain embodiments, the first monoclonal antibody comprises at least one, and preferably 2, 3, or 4 consecutive "critical residues" for binding to IGFBP7. A "critical residue" is defined as an amino acid of SEQ ID NO: 1 (or SEQ ID NO: 2) that, when changed to an alanine, reduces binding of an antibody by at least 50%, and more preferably at least 75%, relative to its binding to SEQ ID NO: 1 (or SEQ ID NO: 2) itself. In preferred embodiments, the at least one critical residue is at least one residue in the sequence TELLPGDRD (SEQ ID NO: 3) or at least one residue in the sequence EPASC (SEQ ID NO: 4).

Such monoclonal antibodies may be conjugated to a signal development element or immobilized on a solid support. In an example of a sandwich assay, a first antibody (detectably labeled) and a second antibody (immobilized at a predetermined zone of a test device) form sandwich complexes with IGFBP7 in the sample at a predetermined zone of a test device. In sandwich assays, the first and second antibodies can be the same (particularly when polyclonal antibodies are used) or different. Thus, the antibodies of the invention may be used in sandwich pairs, or may be used individually with another binding entity which is not a monoclonal antibody such as a polyclonal antibody or an aptamer.

The antibodies of the present invention can be used as reagents in test kits for detecting IGFBP7 in biological samples. Such a test kit may, for example, comprise a disposable test device configured to generate a detectable signal related to the present or amount of human IGFBP7 in a biological sample. Alternatively, such a test kit may be formulated for performing an assay in a clinical analyzer which does not utilize a disposable test device. Preferably, the test kit is an in vitro diagnostic. The term "in vitro diagnostic" as used herein refers to a medical device which is a reagent, reagent product, calibrator, control material, kit, instrument, apparatus, equipment, or system, whether used alone or in combination, intended by the manufacturer to be used in vitro for the examination of specimens, including blood and tissue donations, derived from the human body, solely or principally for the purpose of providing information concerning a physiological or pathological state, or concerning a congenital abnormality, or to determine the safety and compatibility with potential recipients, or to monitor therapeutic measures.

In certain embodiments, the immunoassay is performed in a lateral flow format. Lateral flow tests are a form of immunoassay in which the test sample flows in a chromatographic fashion along a bibulous or non-bibulous porous solid substrate. Lateral flow tests can operate as either competitive or sandwich format assays. Preferred lateral flow devices are disposable, single use test devices. A sample is applied to the test device at an application zone and transits the substrate, where it encounters lines or zones which have been pretreated with an antibody or antigen. The term "test zone" as used herein refers to a discrete location on a lateral flow test strip which is interrogated in order to generate a signal related to the presence or amount of an analyte of interest. The detectable signal may be read visually or obtained by inserting the disposable test device into an analytical instrument such as a reflectometer, a fluorometer, or a transmission photometer. This list is not meant to be limiting. Sample may be applied without pretreatment to the application zone, or may be premixed with one or more assay reagents prior to application. In the latter case, the antibody may be provided in a separate container from the disposable test device.

An antibody of the present invention may be diffusively immobilized to a surface within a disposable test device, such that the antibody dissolves into a sample when the sample contacts the surface. In a sandwich assay format, this diffusively bound antibody may bind to its cognate antigen in the sample, and then be immobilized at a detection zone when the antigen is bound by a second antibody non-diffusively bound at the detection zone. In a competitive format, its cognate antigen in the sample may compete for binding to the diffusively bound antibody with a labeled antigen provided as an assay reagent.

A kit of the invention can further comprise a calibration to relate the detectable signal to a concentration of IGFBP7. By way of example, a calibration curve may be provided on an electronic memory device which is read by the analytical instrument which receives the disposable test device, such as a ROM chip, a flash drive, an RFID tag, etc. Alternatively, the calibration curve may be provided on an encoded label which is read optically, such as a 2-D bar code, or transmitted via a network connection. The analytical instrument can then use this calibration curve to relate a detectable signal from an assay into an IGFBP7 concentration.

In certain embodiment, an assay method performed using the antibody pair of the present invention provides a signal related to the present or amount of human IGFBP7 in a biological sample, wherein the minimum detectable concentration of IGFBP7 in the assay method is 20 ng/mL or less, more preferably 10 ng/mL or less, 5 ng/mL or less, 1 ng/mL or less, and most preferably 0.1 ng/mL or less.

In related aspects, the present invention provides methods for determining the presence or amount of human IGFBP7 in a biological sample, comprising:

performing an immunoassay on the biological sample with a first monoclonal antibody and a second monoclonal antibody which together form sandwich complexes with human IGFBP7, wherein the immunoassay provides a detectable signal that is related to the presence or amount of human IGFBP7 in the biological sample bound in the sandwich complexes; and relating the detectable signal to the presence or amount of human IGFBP7 in the biological sample. Preferably, the minimum detectable concentration of IGFBP7 in the immunoassay is 20 ng/mL or less, more preferably 10 ng/mL or less, 5 ng/mL or less, 1 ng/mL or less, and most preferably 0.1 ng/mL or less.

In particularly preferred embodiments, the first monoclonal antibody binds to a polypeptide consisting of SEQ ID NO: 1, and the second monoclonal antibody binds to the polypeptide consisting of SEQ ID NO: 2, in each case with an affinity of at least $10^8$ $M^{-1}$.

Preferred assay methods comprise performing an immunoassay that detects human IGFBP7. Such immunoassays may comprise contacting said body fluid sample with an antibody that detects the marker, and detecting binding to that antibody. Preferably, the body fluid sample is selected from the group consisting of urine, saliva, blood, serum, and plasma, and most preferably urine.

With regard to the antibodies of the present invention, the invention also relates to nucleic acids encoding such antibodies, and antibody-expressing cell lines expressing such antibodies in additional aspects.

The details of one or more embodiments of the disclosure are set forth in the accompanying drawings and the description below. Other features, objects, and advantages of the disclosure will be apparent from the description and drawings, and from the claims.

DETAILED DESCRIPTION

Definitions

As used herein, the terms "Insulin-like growth factor-binding protein 7" and "IGFBP7" refer to one or more polypeptides present in a biological sample that are derived from the Insulin-like growth factor-binding protein 7 precursor (Swiss-Prot Q16270 (SEQ ID NO: 5))

```
          10         20         30         40
    MERPSLRALL LGAAGLLLLL LPLSSSSSSD TCGPCEPASC 50         60         70         80
    PPLPPLGCLL GETRDACGCC PMCARGEGEP CGGGGAGRGY 90        100        110        120
    CAPGMECVKS RKRRKGKAGA AAGGPGVSGV CVCKSRYPVC 130        140        150        160
    GSDGTTYPSG CQLRAASQRA ESRGEKAITQ VSKGTCEQGP
```

-continued
```
         170        180        190        200
    SIVTPPKDIW NVTGAQVYLS CEVIGIPTPV LIWNKVKRGH 210        220        230        240
    YGVQRTELLP GDRDNLAIQT RGGPEKHEVT GWVLVSPLSK 250        260        270        280
    EDAGEYECHA SNSQGQASAS AKITVVDALH EIPVKKGEGA EL
```

The following domains have been identified in Insulin-like growth factor-binding protein 7:

| Residues | Length | Domain ID |
|---|---|---|
| 1-26 | 26 | Signal peptide |
| 27-282 | 256 | Insulin-like growth factor-binding protein 7 |

Unless specifically noted otherwise herein, the definitions of the terms used are standard definitions used in the art of pharmaceutical sciences. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

The term "lateral flow" as used herein refers to flow of reagents in a longitudinal direction through a substantially flat porous material. Such porous material is "substantially flat" if the thickness of the material is no more than 10% of the length and width dimensions.

The term "downstream region" as used herein relative to a first region of a device refers to which receives fluid flow after that fluid has already reached the first region.

The term "sample application region" as used herein refers to a portion of an assay device into which a fluid sample of interest is introduced for purposes of determining a component thereof.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described marker. The kit comprises reagents for the analysis of at least one test sample which comprise at least one antibody that specifically binds to the marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

In certain embodiments, the marker assay is performed using a single-use disposable test device. Such test devices often take the form of lateral flow devices which are now familiar from the common use of over-the-counter pregnancy tests. Generally, these assay devices have an extended base layer on which a differentiation can be made between a sample addition region and an evaluation region. In typical use, the sample is applied to the sample addition region, flows along a liquid transport path which runs parallel to the base layer, and then flows into the evaluation region. A capture reagent is present in the evaluation region, and the captured analyte can be detected by a variety of protocols to detect visible moieties associated with the captured analyte. For example, the assay may produce a visual signal, such as color change, fluorescence, luminescence, and the like, when indicating the presence or absence of an analyte in a biological sample.

A sample addition region can be provided, for example, in the form of an open chamber in a housing; in the form of an absorbent pad; etc. The sample addition region can be a port of various configurations, that is, round, oblong, square and the like or the region can be a trough in the device.

A filter element can be placed in, on, or adjacent to the sample addition region to filter particulates from the sample, such as to remove or retard blood cells from blood so that plasma can further travel through the device. Filtrate can then move into a porous member fluidly connected to the filter. Suitable filters for removing or retarding cellular material present in blood are well known in the art. See, e.g., U.S. Pat. Nos. 4,477,575; 5,166,051; 6,391,265; and 7,125,493, each of which is hereby incorporated by reference in its entirety. Many suitable materials are known to skilled artisans, and can include glass fibers, synthetic resin fibers, membranes of various types including asymmetric membrane filters in which the pore size varies from about 65 to about 15 µm, and combinations of such materials. In addition, a filter element can comprise one or more chemical substances to facilitate separation of red blood cells from blood plasma. Examples of such chemical substances are thrombin, lectins, cationic polymers, antibodies against one or more red blood cell surface antigens and the like. Such chemical substance(s) which facilitate separation of red blood cells from plasma may be provided in the filter element by covalent means, nonspecific absorption, etc.

In certain embodiments, a label zone is located downstream of the sample receiving zone, and contains a diffusively located labeled reagent that binds to the analyte of interest or that competes with the analyte of interest for binding to a binding species. Alternatively, the label zone can be eliminated if the labeled reagent is premixed with the sample prior to application to the sample receiving zone. A detection zone is disposed downstream of from the label zone, and contains an immobilized capture reagent that binds to the analyte of interest.

The optimum pore diameter for the membrane for use in the invention is about 10 to about 50 µm. The membranes typically are from about 1 mil to about 15 mils in thickness, typically in the range of from 5 or 10 mils, but may be up to 200 mils and thicker. The membrane may be backed by a generally water impervious layer, such as a Mylar® polyester film (DuPont Teijin Films). When employed, the backing is generally fastened to the membrane by an adhesive, such as 3M 444 double-sided adhesive tape. Typically, a water impervious backing is used for membranes of low thickness. A wide variety of polymers may be used provided that they do not bind nonspecifically to the assay components and do not interfere with flow of the sample. Illustrative polymers include polyethylene, polypropylene, polystyrene and the like. Alternatively, the membrane may be self supporting. Other non-bibulous membranes, such as polyvinyl chloride, polyvinyl acetate, copolymers of vinyl acetate and vinyl chloride, polyamide, polycarbonate, polystyrene, and the like, can also be used. In various embodiments, the label zone material may be pretreated with a solution that includes blocking and stabilizing agents. Blocking agents include bovine serum albumin (BSA), methylated BSA, casein, nonfat dry milk. The device can also comprise additional components, including for example buffering agents, HAMA inhibitors, detergents, salts (e.g., chloride and/or sulfate salts of calcium, magnesium, potassium, etc.), and proteinaceous components (e.g., serum albumin, gelatin, milk proteins, etc.). This list is not meant to be limiting.

The device may further comprise various control locations which are read to determine that the test device has been run properly. By way of example, a procedural control zone may be provided separate from the assay detection zone to verify that the sample flow is as expected. The control zone is preferably a spatially distinct region at which a signal may be generated that is indicative of the proper flow of reagents. The procedural control zone may contain the analyte of interest, or a fragment thereof, to which excess labeled antibody used in the analyte assay can bind. In operation, a labeled reagent binds to the control zone, even when the analyte of interest is absent from the test sample. The use of a control line is helpful in that appearance of a signal in the control line indicates the time at which the test result can be read, even for a negative result. Thus, when the expected signal appears in the control line, the presence or absence of a signal in the capture zone can be noted. The device may further comprise a negative control area. The purpose of this control area is to alert the user that the test device is not working properly. When working properly, no signal or mark should be visible in the negative control area.

The outer casing or housing of such an assay device may take various forms. Typically, it will include an elongate casing and may have a plurality of interfitting parts. In a particularly preferred embodiment, the housing includes a top cover and a bottom support. The top cover contains an application aperture and an observation port. In a preferred embodiment, the housing is made of moisture impervious solid material, for example, a plastic material. It is contemplated that a variety of commercially available plastics, including, but not limited to, vinyl, nylon, polyvinyl chloride, polypropylene, polystyrene, polyethylene, polycarbonates, polysulfanes, polyesters, urethanes, and epoxies maybe used to construct a housing. The housing may be prepared by conventional methodologies, such as standard molding technologies that are well known and used in the art. The housing may be produced by molding technologies which include, but are not limited to, injection molding, compression molding, transfer molding, blow molding, extrusion molding, foam molding, and thermoform molding. The aforementioned molding technologies are well known in the art and so are not discussed in detail herein. See for example, Processes And Materials Of Manufacture, Third Edition, R. A. Lindsberg (1983) Allyn and Baron pp. 393-431.

If necessary, the colorimetric, luminescent, or fluorescent intensity of the detectable label being employed may be then evaluated with an instrument that is appropriate to the label. By way of example, a fluorometer can be used to detect fluorescent labels; a reflectometer can be used to detect labels which absorb light, etc. The concentration of the analyte of interest in the samples may be determined by correlating the measured response to the amount of analyte in the sample fluid.

Assay Correlations

The terms "correlating" and "relating" as used herein in reference to the measurement of biomarkers in an assay refers to determining the presence, or more preferably the amount, of the biomarker in a sample based on the signal obtained from the assay. Often, this takes the form of comparing a signal generated from a detectable label on one species participating in the assay to a predetermined standard curve which can be used to convert the signal to a concentration or threshold amount of the biomarker.

The terms "correlating" and "relating" as used herein in reference to the use of biomarkers for diagnosis or prognosis refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., Intensive Care Med. 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Ordinarily, an antibody may comprise heavy and/or light chain variable comprising an amino acid sequence having at least 75% amino acid sequence identity or similarity with the amino acid sequence of either the heavy or light chain variable domain of a parent antibody having known binding characteristics, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

While conservative substitutions are often preferred, non-conservative substitutions (which entail exchanging a member of one of these classes for a member of another class) are also contemplated.

Preferred therapeutic antibodies are IgG antibodies. The term "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. The known Ig domains in the IgG class of antibodies are VH, Cγ1, Cγ2, Cγ3, VL, and CL. IgG is the preferred class for therapeutic antibodies for several practical reasons. IgG antibodies are stable, easily purified, and able to be stored under conditions that are practical for pharmaceutical supply chains. In vivo they have a long biological half-life that is not just a function of their size but is also a result of their interaction with the so-called Fc receptor (or FcRn). This receptor seems to protect IgG from catabolism within cells and recycles it back to the plasma.

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d=k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

Antibodies of the invention may be further characterized by epitope mapping, so that antibodies and epitopes may be selected that have the greatest clinical utility in the immunoassays described herein. The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Preferably, an epitope is targeted which is present on the target molecule, but is partially or totally absent on non-target molecules.

In some embodiments, the antibody scaffold can be a mixture of sequences from different species. As such, if the antibody is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res.57 (20):4593-9; Gorman et al., 1991, Proc. Natl. Acad. Sci. USA 88:4181-4185; O'Connor et al., 1998, Protein Eng 11:321-8. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084.

In one embodiment, the antibody is a fully human antibody. "Fully human antibody" or "complete human antibody" refers to a human antibody having the gene sequence of an antibody derived from a human chromosome. Fully human antibodies may be obtained, for example, using transgenic mice (Bruggemann et al., 1997, Curr Opin Biotechnol 8:455-458) or human antibody libraries coupled with selection methods (Griffiths et al., 1998, Curr Opin Biotechnol 9:102-108).

Production of Antibodies

Monoclonal antibody preparations can be produced using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Monoclonal antibodies derived from animals other than rats and mice offer unique advantages. Many protein targets relevant to signal transduction and disease are highly conserved between mice, rats and humans, and can therefore be recognized as self-antigens by a mouse or rat host, making them less immunogenic. This problem may be avoided when using rabbit as a host animal. See, e.g., Rossi et al., *Am. J. Clain. Pathol.*, 124, 295-302, 2005.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Adjuvants that can be used in the methods of antibody generation include, but are not limited to, protein adjuvants; bacterial adjuvants, e.g., whole bacteria (BCG, *Corynebacterium parvum, Salmonella minnesota*) and bacterial components including cell wall skeleton, trehalose dimycolate, monophosphoryl lipid A, methanol extractable residue (MER) of tubercle bacillus, complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used in the methods of the invention include, Cholera toxin, paropox proteins, MF-59 (Chiron Corporation; See also Bieg et al. (1999) "GAD65 And Insulin B Chain Peptide (9-23) Are Not Primary Autoantigens In The Type 1 Diabetes Syndrome Of The BB Rat," Autoimmunity, 31(1):15-24, which is incorporated herein by reference), MPL® (Corixa Corporation; See also Lodmell et al. (2000) "DNA Vaccination Of Mice Against Rabies Virus: Effects Of The Route Of Vaccination And The Adjuvant Monophosphoryl Lipid A (MPL)," Vaccine, 18: 1059-1066; Johnson et al. (1999) "3-O-Desacyl Monophosphoryl Lipid A Derivatives: Synthesis And Immunostimulant Activities," Journal of Medicinal Chemistry, 42: 4640-4649; Baldridge et al. (1999) "Monophosphoryl Lipid A (MPL) Formulations For The Next Generation Of Vaccines," Methods, 19: 103-107, all of which are incorporated herein by reference), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al. (1998) "Active Immunotherapy With Ultraviolet B-Irradiated Autologous Whole Melanoma Cells Plus DETOX In Patients With Metastatic Melanoma," Clin. Cancer Res. 4(3):619-627; and Gupta et al. (1995) "Adjuvants For Human Vaccines—Current Status, Problems And Future Prospects," Vaccine, 13(14): 1263-1276, both of which are incorporated herein by reference).

Numerous publications discuss the use of phage display technology to produce and screen libraries of polypeptides for binding to a selected analyte. See, e.g, Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. (1995) "Human Antibodies From Transgenic Mice," Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

Recombinant Expression of Antibodies

Once a nucleic acid sequence encoding an antibody of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. (See, for example, the techniques described in Sambrook et al, 1990, MOLECULAR CLONING, A LABORATORY MANUAL, 2d Ed., Cold Spring Harbor Laboratory, Cold Spring Harbor, N.Y. and Ausubel et al. eds., 1998, CURRENT PROTOCOLS IN MOLECULAR BIOLOGY, John Wiley & Sons, NY).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The host cells used to express the recombinant antibodies of the invention may be either bacterial cells such as Escherichia coli, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors." Gene 45:101-105; Cockett et al. (1990) "High Level Expression Of Tissue Inhibitor Of Metalloproteinases In Chinese Hamster Ovary Cells Using Glutamine Synthetase Gene Amplification," Biotechnology 8:662-667).

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., E. coli and B. subtilis) transformed with recombinant bacteriophage DNA, plasmid DNA or cosmid DNA expression vectors containing immunoglobulin coding sequences; yeast (e.g., Saccharomyces pichia) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807, 715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the E. coli expression vector pUR278 (Ruther et al. (1983) "Easy Identification Of cDNA Clones," EMBO J. 2:1791-1794), in which the antibody coding sequence may be ligated individually into the vector in frame with the lac Z coding region so that a fusion protein is produced; pIN vectors (Inouye et al. (1985) "Up-Promoter Mutations In The Lpp Gene Of Escherichia coli," Nucleic Acids Res. 13:3101-3110; Van Heeke et al. (1989) "Expression Of Human Asparagine Synthetase In Escherichia coli," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region El or E3) will result in a recombinant virus that is viable and capable of expressing the immunoglobulin molecule in infected hosts. (see e.g., see Logan et al. (1984) "Adenovirus Tripartite Leader Sequence Enhances Translation Of mRNAs Late After Infection," Proc. Natl. Acad. Sci. (U.S.A.) 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11:223-232), hypoxanthine-guanine phosphoribosyltransferase (Szybalska et al. (1962) "Genetics Of Human Cess Line. IV. DNA-Mediated Heritable Transformation Of A Biochemical Trait," Proc. Natl. Acad. Sci. (U.S.A.) 48:2026-2034), and adenine phosphoribosyltransferase (Lowy et al. (1980) "Isolation Of Transforming DNA: Cloning The Hamster Aprt Gene," Cell 22:817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplfiable Dominant-Acting Gene," Proc. Natl. Acad. Sci. (U.S.A.) 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. (U.S.A.) 78:1527-1531); gpt, which confers resistance to mycophenolic acid (Mulligan et al. (1981) "Selection For Animal Cells That Express The Escherichia coli Gene Coding For Xanthine-Guanine Phosphoribosyltransferase," Proc. Natl. Acad. Sci. (U.S.A.) 78:2072-2076); neo, which confers resistance to the aminoglycoside G-418 (Tachibana et al. (1991) "Altered Reactivity Of Immunoglobutin Produced By Human-Human Hybridoma Cells Transfected By pSV2-Neo Gene," Cytotechnology 6(3):219-226; Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human gene therapy," Ann. Rev. Biochem. 62:191-217). Methods commonly known in the art of recombinant DNA technology which can be used are described in Ausubel et al. (eds.), 1993, CURRENT PROTOCOLS IN MOLECULAR BIOLOGY, John Wiley & Sons, NY; Kriegler, 1990, GENE TRANSFER AND EXPRESSION, A LABORATORY MANUAL, Stockton Press, NY; and in Chapters 12 and 13, Dracopoli et al. (eds), 1994, CURRENT PROTOCOLS IN HUMAN GENETICS, John Wiley & Sons, NY.; Colbere-Garapin et al. (1981) "A New Dominant Hybrid Selective Marker For Higher Eukaryotic Cells," J. Mol. Biol. 150:1-14; and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156).

The expression levels of an antibody of the invention can be increased by vector amplification (for a review, see Bebbington and Hentschel, "The Use Of Vectors Based On Gene Amplification For The Expression Of Cloned Genes In Mammaian Cells," in DNA CLONING, Vol. 3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al. (1983) "Expression And Amplification Of Engineered Mouse Dihydrofolate Reductase Minigenes," Mol. Cell. Biol. 3:257-266).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot (1986) "Expression And Amplification Of Engineered Mouse Dihydrofolate Reductase Minigenes," Nature 322:562-565; Kohler (1980) "Immunoglobulin Chain Loss In Hybridoma Lines," Proc. Natl. Acad. Sci. (U.S.A.) 77:2197-2199). The coding sequences for the heavy and light chains may comprise cDNA or genomic DNA.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

EXAMPLES

Example 1

Monoclonal Antibody Development in Rabbits

Female New Zealand Rabbits were immunized by subcutaneous injections (SQ) with antigen/adjuvant emulsions. Primary immunization was done with Complete Freund's Adjuvant and Incomplete Freund's Adjuvant was used for all subsequent boosts. Rabbits were injected SQ every three weeks at 250 μg protein antigen per rabbit (alternating two sites, hips and scapulas). A test bleed was taken from the marginal ear vein seven days after the second boost. This test bleed (immune sera) was tested by indirect ELISA assay to determine if immune response of the rabbit was adequate for monoclonal antibody development. The best responding rabbit was given a final SQ boost and four days later was euthanized via exsanguination. The whole blood was collected via cardiac puncture. B cells producing antibody of interest were identified by indirect ELISA on target antigen and immunoglobulin genes were isolated. Heavy and light chains were cloned into separate mammalian expression vectors, transfected into HEK cells (transient transfection), and tissue culture supernatant containing rabbit monoclonal antibodies were harvested.

Example 2

Monoclonal Antibody Development in Mice

Female BALB/c mice (60 days old) were immunized by intraperitoneal injections (IP) with antigen/adjuvant emulsions as per standard operating procedure. Primary immunization was done with Complete Freund's Adjuvant and Incomplete Freund's Adjuvant was used for all subsequent boosts. Mice were injected IP every 3 weeks at 25 μg antigen per mouse (total volume 125 μL per mouse). Test bleeds were done by saphenous vein lancing 7 to 10 days after the second boost. This test bleed (immune sera) was tested by indirect ELISA assay to determine if the immune response of mice was adequate for fusion. The best 2 responding mice were given a final intravenous boost of 10 μg antigen per mouse in sterile saline via lateral tail vein. 4 days after the IV boost the mice were euthanized and the spleens were harvested. Lymphocytes isolated from the spleen were used in the fusion process to produce hybridomas using the method of Kohler, G.; Milstein, C. (1975). "Continuous cultures of fused cells secreting antibody of predefined specificity". Nature 256 (5517): 495-497. Hybridomas were generated using a PEG1500 fusion process.

Example 3

Screening of Antibodies with Patient Samples (Microtiter-based ELISA Method)

Materials:
96-well high bind ELISA plates-Costar 3590 (Corning)
ELISA coating buffer: PBS
ELISA wash buffer: PBS with 0.02% Tween-20
ELISA blocking Buffer (Thermo Pierce, catalogue number N502)
ELISA reagent diluent: 200 mM Tris, 1% BSA (BioFx), 0.05% Tween-20, pH 8.1
Neutravidin-HRP conjugate (Thermo Pierce, catalogue number 31001)
1-Step Ultra TMB substrate (R&D systems, catalogue number 34028)
Stop solution: 2N sulfuric acid
Capture antibodies
Biotin conjugated detection antibodies
Recombinant human IGFBP7 (Peprotech, catalogue number 410-02)
EXLx405 plate washer (Biotek)
Multiskan FC plate reader (Fisher Scientific)

Testing Procedure

Purified, recombinant IGFBP7 analyte was spiked into Reagent Diluent and serially diluted to generate a set of standard samples covering a range of concentrations. Frozen single-use aliquots of patient samples were thawed in a room temperature water bath for 10 minutes, and then diluted to desired level with Reagent Diluent.

100 μL of 5 μg/mL Capture Antibody solution prepared in coating buffer was added to each well on a 96-well high bind ELISA plate and incubated over night at room temperature (22° C. to 25° C.). Each well was aspirated and washed three times with 300 μL of wash buffer using an autowasher. Then 250 μL of ELISA blocking buffer was added to each well. After an incubation of 2 hours at room temperature, the aspiration/wash step described above was repeated.

100 μL of standard or patient samples was added to each well of the prepared plate and incubated at room temperature on a horizontal orbital shaker. After 2 hours of incubation, the plate was washed as described above. Then 100 μL of 0.1 μg/mL detection antibody solution prepared in reagent diluent was added to each well. After incubation for 1 hour at room temperature, the plate was washed again. A 0.1 μg/mL solution of neutravidin-HRP conjugate was prepared in reagent diluent, and 100 μL of this solution was added to each well. The plate was incubated for 1 hour at room temperature and washed. 100 μL of 1-step ultra TMB substrate was added to each well, incubated at room temperature for 10 minutes protected from light, followed by 50 μL of stop solution. The optical density in each well was measured with a microplate reader set to a wavelength of 450nm.

Example 4

Screening of Antibodies with Patient Samples (Lateral Flow Strip Testing Method)

Materials:
Nitrocellulose membrane
Backing card
Sample pad
Wicking pad
Membrane blocking buffer: 10 mM Sodium phosphate, 0.1% sucrose, 0.1% BSA, 0.2% PVP-40, pH 8.0
Sample pad blocking buffer: 5 mM Borate, 0.1% Tween-20, 0.25% PVP-40, 0.5% BSA, pH 8.5
Running buffer J: 500 mM Tris, 0.2% 10G, 0.35% Tween-20, 0.25% PVP-40, pH 8.5
Fluorescently-conjugated antibodies
Test line antibodies
Goat-anti-mouse positive control antibodies
Recombinant human IGFBP7

Strip Assembly

Nitrocellulose membranes were striped with test line antibodies using an AD3050 aspirate dispense system, blocked with the membrane blocking buffer and dried at 37° C. for 30 min. After curing over night in a desiccator, the striped and blocked nitrocellulose membranes were laminated onto backing cards with wicking pads and sample pads pre-treated with the sample pad blocking buffer. The cards were cut into 5 mm wide test strips, which were then placed into cartridges.

Sample Preparation

Purified, recombinant IGFBP7 analyte was spiked into Running buffer J and serially diluted to generate a set of standard samples covering a range of concentrations. Frozen single-use aliquots of patient samples were thawed in a room temperature water bath for 10 minutes, and then diluted to desired level with Running buffer J.

Testing Procedure

10 μL of fluorescently conjugated antibody (0.025 μg/μL) in PBS was added to 100 μL of sample. 100 μL of this solution was then loaded into the input port on the cartridge. Results was read at t=20 minutes using a fluorescence reader and associated software.

Example 5

Peptide Mapping

Materials: 96-well high bind microtiter plates, Neutravidin, biotinylated peptides, Unconjugated antibodies, mouse IgG, rabbit IgG, goat IgG, HRP conjugated to anti-mouse IgG HRP conjugate, anti-rabbit IgG HRP conjugate, anti-goat IgG HRP conjugate, TMB substrate, 2N sulfuric acid were used for epitope mapping experiments.

Neutravidin was immobilized in individual wells of 96-well high bind microtiter plate. The plates were washed to remove unreacted neutravidin followed by a blocking step. Biotinylated peptides were dissolved in an aqueous buffer to a concentration of 10 μg/mL. 50 μL of the peptide solutions were added to each well of neutravidin coated microtiter plates. These plates were incubated one hour at room temperature and then washed to remove unbound peptides. Unconjugated mouse and rabbit antibodies were diluted to 5 μg/mL and added to the plate at 100 μL/well. Anti-mouse IgG (in the mouse anti-IGFBP7) or anti-rabbit IgG (in the case of rabbit anti-IGFBP7) was added to neighboring wells as a negative control. Plates were incubated 1 hour at room temperature and washed. HRP conjugated to anti-mouse IgG (in the case of mouse anti-IGFBP7 and mouse IgG negative control), and HRP conjugated to anti-rabbit IgG (in the case of rabbit anti-IGFBP7 and rabbit IgG negative control) was diluted to 0.2 μg/mL and 100 μL was added to each well of the plate. These plates were incubated for 20 minutes at room temperature and washed. 100 μL/well of TMB substrate was added and plates were incubated for 20 minutes while avoiding exposure to light. 50 μl/well of Stop solution (2N sulfuric acid) was added to each well and plates to stop the reaction. The absorbance was read on spectrophtometric 96-well microplate reader set to measure the optical density at 450 nm.

Example 6

Alanine Scanning Peptide Mapping

Alanine scanning is a widely used mutagenesis approach in which residues in a target protein are systematically substituted for alanine at selected positions by site-directed mutagenesis, expressed, and assayed for function. Substitution with alanine residues eliminates side-chain interactions without altering main-chain conformation or introducing steric or electrostatic effects. Using automated mutagenesis protocols, every residue in a target polypeptide is changed to alanine, and critical residues that comprise each antibody binding domain can be determined.

Example 7

Results

Using the combined alanine scanning and peptide mapping results, unique IGFBP7 monoclonal antibodies were identified and selected based on analytical performance.

| Antibody | Pepscan sequence | Astute Sequence (total region) |
|---|---|---|
| 7G2.1 | $_{210}$PGDRD$_{214}$ (SEQ ID NO: 6) | $_{201}$YGVQRTELLPGDRDNL$_{216}$ (SEQ ID NO: 6) |
| 6D2.1 | $_{206}$TELLPGDR$_{213}$ (SEQ ID NO: 3) | $_{191}$LIWNKVKRGHYGVQRT$_{206}$ (SEQ ID NO: 7) |
| 1C9E4.1 | $_{36}$EPASC$_{40}$ (SEQ ID NO: 4) | $_{25}$SSSSSDTCGPCEPASCPPLP$_{44}$ (SEQ ID NO: 8) |

Example 8

Sequencing Data

Antibody IC9E4.1 was isotyped as a murine IgG1/kappa antibody. cDNA from the monoclonal cell line was obtained for sequencing by standard methods. The sequences of the heavy chain variable region and the light chain variable region were as follows:

$V_{light}$
(SEQ ID NO: 9)
```
DVVMTQTPLT LSVTIGQPAS ISCKSSQSLL YSNGETYLHW LLQRPGQSPK    50
RLIYLVSKLD SGVPDRFTGS GSRTDFTLKI SRVEAEDLGV YYCAQGTHFP   100
HTFGGGTKLE
```

$V_{heavy}$
(SEQ ID NO: 10)
```
QIQLVQSGPE LKKPGETVKI SCKASGYSFT DYSIHWVKQA PGKGLKWMGL    50
INTETGEPIY VDDFKGRFAF SLETSARTAY LQINNLKNED TATYFCARAY   100
YWAYWGQGTL V
```

Antibody 1D6

Antibody 1D6 was isotyped as a murine IgG1/kappa antibody. By epitope mapping, the 1D6 antibody was determined to bind to a conformational epitope of IGFBP7. cDNA from the monoclonal cell line was obtained for sequencing by standard methods. The sequences of the heavy chain variable region and the light chain variable region were as follows:

V<sub>light</sub>

(SEQ ID NO: 11)
```
QIVLTQSPAI MSASPGEKVT MTCSASSSVS YMHWYQQKSG TSPKRWIYDT     50

SELASGVPAR FSGSGSGTSY SLTISSMEAE DAATYYCQQW SSSPFTFGSG    100

TKLEIKR
```

V<sub>heavy</sub>

(SEQ ID NO: 12)
```
QIQLVQSGPE LKKPGETVKI SCKASGYTFK KYGMNWVKQA PGKGLKWMGW     50

INTYTGEPIY ADDFKGRFAF SLETSASTAY LQISNLKNED TATYFCAREE

YGPFYAMDYW GQGTSVTVSS
```

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The use of "or" herein means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. All patents and publications mentioned in the specification are indicative of the levels of those of ordinary skill in the art to which the invention pertains prior to the filing date of the disclosure. Nothing herein is to be construed as an admission that the inventors are not entitled to antedate such disclosure by virtue of prior disclosure.

It will be readily apparent to a person skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. An isolated antibody that binds to a human IGFBP7 protein, wherein the antibody comprises three complementarity determining regions of a light chain variable region having the amino acid sequence of SEQ ID NO: 9 and three complementarity determining regions of a heavy chain variable region having the amino acid sequence of SEQ ID NO: 10, wherein the complementarity determining regions are defined according to Kabat.

2. The antibody according to claim 1, wherein the antibody is a monoclonal antibody.

3. The isolated antibody according to claim 1, wherein the antibody is conjugated to a signal development element.

4. The isolated antibody according to claim 1, wherein the antibody is conjugated to a solid support.

5. An immunoassay method for detecting the presence or amount of human IGFBP7, comprising:
   contacting a sample with the antibody according to claim 1;
   detecting binding of the human IGFBP7 in the sample to the antibody; and
   relating the detected binding to the presence or amount of the human IGFBP7.

6. A nucleic acid encoding an antibody that binds to a human IGFBP7 protein, wherein the antibody comprises three complementarity determining regions of a light chain variable region having the amino acid sequence of SEQ ID NO: 9 and three complementarity determining regions of a heavy chain variable region having the amino acid sequence of SEQ ID NO: 10, wherein the complementarity determining regions are defined according to Kabat.

7. An antibody-expressing cell line, the cell line expressing an antibody that binds to a human IGFBP7 protein and comprises three complementarity determining regions of a light chain variable region having the amino acid sequence of SEQ ID NO: 9 and three complementarity determining regions of a heavy chain variable region having the amino acid sequence of SEQ ID NO: 10, wherein the complementarity determining regions are defined according to Kabat.

8. An isolated antibody that binds to a human IGFBP7protein, wherein the antibody comprises three complementarity determining regions of a light chain variable region having the amino acid sequence of SEQ ID NO: 11 and three complementarity determining regions of a heavy chain variable region having the amino acid sequence of SEQ ID NO: 12, wherein the complementarity determining regions are defined according to Kabat.

9. The antibody according to claim 8, wherein the antibody is a monoclonal antibody.

10. The isolated antibody according to claim 8, wherein the antibody is conjugated to a signal development element.

11. The isolated antibody according to claim 8, wherein the antibody is conjugated to a solid support.

12. An immunoassay method for detecting the presence or amount of human IGFBP7, comprising:
    contacting a sample with the antibody according to claim 8;
    detecting binding of the human IGFBP7 in the sample to the antibody; and
    relating the detected binding to the presence or amount of the human IGFBP7.

13. A nucleic acid encoding an antibody that binds to a human IGFBP7 protein, wherein the antibody comprises three complementarity determining regions of a light chain variable region having the amino acid sequence of SEQ ID NO: 11 and three complementarity determining regions of a heavy chain variable region having the amino acid sequence of SEQ ID NO: 12, wherein the complementarity determining regions are defined according to Kabat.

14. An antibody-expressing cell line, the cell line expressing an antibody that binds to a human IGFBP7 protein and comprises three complementarity determining regions of a light chain variable region having the amino acid sequence of SEQ ID NO: 11 and three complementarity determining regions of a heavy chain variable region having the amino acid sequence of SEQ ID NO: 12, wherein the complementarity determining regions are defined according to Kabat.

\* \* \* \* \*

UNITED STATES PATENT AND TRADEMARK OFFICE
CERTIFICATE OF CORRECTION

PATENT NO. : 10,562,961 B2
APPLICATION NO. : 15/818669
DATED : February 18, 2020
INVENTOR(S) : Ravi A. Vijayendran and Srivatsa Venkatasubbarao It is certified that error appears in the above-identified patent and that said Letters Patent is hereby corrected as shown below:

In the Claims

At Claim 8, Column 36, Line 25, the text "IGFBP7protein, wherein the antibody comprises three" should be changed to --IGFBP7 protein, wherein the antibody comprises three--

Signed and Sealed this
Thirty-first Day of March, 2020

Andrei Iancu
*Director of the United States Patent and Trademark Office*